US009618428B2

(12) United States Patent
Horton et al.

(10) Patent No.: US 9,618,428 B2
(45) Date of Patent: Apr. 11, 2017

(54) BIOMETRIC DEVICE AND MEANS FOR ELECTRONIC STORAGE AND RETRIEVAL OF BIOMETRIC DATA

(71) Applicant: GE HEALTHCARE UK LIMITED, Little Chalfont (GB)

(72) Inventors: Jeffrey Kenneth Horton, Cardiff (GB); Peter James Tatnell, Cardiff (GB); Samantha Jane Ogden, Cardiff (GB); Michael John Smith, Cardiff (GB); Leonard J. Goren, Piscataway, NJ (US); Steven Pepe, Trevose, PA (US); Samit Langar, Bangalore (IN); Vincent Francis Pizzi, Millis, MA (US); Craig Robinson, Westborough, MA (US)

(73) Assignee: GE HEALTHCARE UK LIMITED, Little Chalfont (GB)

( * ) Notice: Subject to any disclaimer, the term of this patent is extended or adjusted under 35 U.S.C. 154(b) by 145 days.

(21) Appl. No.: 13/766,954

(22) Filed: Feb. 14, 2013

(65) Prior Publication Data
US 2014/0154686 A1    Jun. 5, 2014

(30) Foreign Application Priority Data

Nov. 30, 2012  (GB) .................................. 1221603.2

(51) Int. Cl.
| | | |
|---|---|---|
| *G06F 19/00* | (2011.01) | |
| *G01N 1/28* | (2006.01) | |
| *G01N 33/558* | (2006.01) | |
| *B01L 3/00* | (2006.01) | |
| *G01N 31/00* | (2006.01) | |

(52) U.S. Cl.
CPC .............. *G01N 1/28* (2013.01); *B01L 3/5055* (2013.01); *G01N 33/558* (2013.01); *B01L 2300/022* (2013.01); *B01L 2300/12* (2013.01)

(58) Field of Classification Search
CPC ................................ G01N 1/28; G01N 33/558
See application file for complete search history.

(56) References Cited

U.S. PATENT DOCUMENTS

| | | | |
|---|---|---|---|
| 4,683,202 A | | 7/1987 | Mullis |
| 5,496,562 A | | 3/1996 | Burgoyne |
| 5,593,824 A | | 1/1997 | Treml et al. |
| 5,763,157 A | | 6/1998 | Treml et al. |
| 5,939,252 A | * | 8/1999 | Lennon et al. ................... 435/4 |
| 6,368,674 B1 | * | 4/2002 | Loewy et al. ................ 427/469 |
| 7,032,818 B2 | * | 4/2006 | Thomas et al. ............... 235/381 |
| 7,191,777 B2 | * | 3/2007 | Brand et al. ............. 128/200.23 |
| 7,382,258 B2 | | 6/2008 | Oldham et al. |
| 7,638,099 B2 | * | 12/2009 | Lloyd et al. .................. 422/537 |
| 7,793,109 B2 | * | 9/2010 | Ortiz ............................. 713/186 |
| 2002/0122852 A1 | * | 9/2002 | Zimmerman et al. ........ 426/285 |
| 2003/0215369 A1 | | 11/2003 | Eggers et al. |
| 2005/0051614 A1 | | 3/2005 | Albany et al. |
| 2008/0176209 A1 | | 7/2008 | Muller et al. |
| 2009/0298132 A1 | | 12/2009 | Muller-Cohn et al. |
| 2009/0318751 A1 | | 12/2009 | Lansdowne |
| 2011/0199187 A1 | | 8/2011 | Davidowitz |
| 2011/0212859 A1 | | 9/2011 | O'Banion et al. |

FOREIGN PATENT DOCUMENTS

| | | |
|---|---|---|
| EP | 1 563 091 | 1/2009 |
| WO | WO 90/03959 | 4/1990 |

OTHER PUBLICATIONS

GB1221603.2 Search Report Dated Apr. 17, 2013.

* cited by examiner

*Primary Examiner* — Eric S Dejong
(74) *Attorney, Agent, or Firm* — Eversheds Sutherland (US) LLP

(57) ABSTRACT

There is disclosed a biometric device (10), comprising a solid support (14) suitable for receiving biological material (S) and for dry storing that material at room temperature the device further comprising a circuit (16) including means for two way radio frequency communication and including writable data storage. Also disclosed is a processing method for such biometric devices, the method including the steps of: a) identifying said device by means of RF communication; b) extracting at least a portion of the biological material from the solid support of the identified device; c) analyzing the extracted biological material to obtain biometric data indicative of the biological material; and d) writing said biometric data to the data storage of the biometric device.

3 Claims, 3 Drawing Sheets

BIOMETRIC DEVICE AND MEANS FOR ELECTRONIC STORAGE AND RETRIEVAL OF BIOMETRIC DATA

FIELD OF THE INVENTION

This invention relates to the collection, and use of biological material, such as nucleic acids or proteins, for conversion into biological information and the use of this information in a readily accessible or retrievable form, for example, in the identification of individuals, in predispositions to diseases, or in disease detection.

In this specification, biological material means any biological matter; biological information means the information obtainable from the biological matter, and biological data means the electronic expression of that information. Likewise genetic/nucleic acid material, information, and data have equivalent meanings.

This invention relates also to a biometric device, and a method of employing the device, including the collection, storage and retrieval of the biological material. One use of this device is the possible confirmation of an individual's identity through the use of the nucleic acids to generate a personal profile. This profile may be converted to genetic information, and stored locally as electronic data, and/or, additionally a link can be made with personally identifiable information which can be used to uniquely identify, contact, or locate a single person or can be used with other sources to uniquely identify a single individual. Suitable personally identifiable information may take the form of:—full name, address, national identification (insurance) number, IP address, vehicle registration plate number, driver's license number, image of an individual's face, fingerprints, or handwriting, credit card numbers, digital identity, date of birth, birthplace and genetic history and so on.

The invention is also concerned with solid support matrices, such as cellulose-based paper (such as a chemically modified or unmodified paper). The solid support matrices are used for the long-term, room temperature, storage, recovery and further processing of the biological material, such as nucleic acids. Herein, room temperature means a temperature between 4° C. and 50° C. This invention is particularly useful in genotyping, diagnostics and, predominantly, forensics applications, with amplification of low copy number genes or low expression mRNA; short tandem repeats (STRs), alleles, loci, or other genetic materials, derived from crude biological samples.

BACKGROUND OF THE INVENTION

This invention has the potential for wide applicability, but in one embodiment, describes the collection and storage of biological material, in particular, genetic material, and the populating of a biometric device for use in the timely identification of individuals. Organisations, particularly those having a global reach (e g military forces, global companies etc.), face difficult and serious challenges concerning the safety of troops and employees facing battlefield scenarios, natural disasters, air crashes, kidnapping and terrorism. In each of these cases, it can be difficult to identify individuals so that remains may be returned to next of kin, insurance claims processed and estates settled. In some instances, due to severity of injuries, there is little information to identify the deceased or victim. Therefore there is an improved need to rapidly identify human remains and individuals. An objective of the present invention is to provide a more reliable way of identifying remains of an individual.

Conventionally, this is achieved by storage and retrieval of genetic material. The genetic material could include a blood spot or cells transferred from buccal swab from an individual's mouth and the genetic material may be stored on the card. The inventors have found that significant improvements in data confidence and processability can be made by employing electronic data storage adjacent the solid support on which the biological material is stored e.g. a radio-frequency identification (RFID) 'tag' capable of receiving, storing and/or sending personal information or genetic data to a remote receiver. Examples of personal information are sex, ethnicity, religion, blood group, tissue (HLA) type and so on.

Biometrics (or biometric authentication) refers to the identification of humans by their characteristics or traits. The benefit of using DNA as a biometric identifier is the level of accuracy offered: the chance of two individuals sharing the same DNA profile is less than one in a 100 billion when 26 short tandem repeats (STR) of nucleic acids are used.

Molecular and Nucleic Acid Analysis

The polymerase chain reaction (PCR) is a common tool used in molecular biology for amplifying nucleic acids. U.S. Pat. No. 4,683,202 (Mullis, Cetus Corporation) describes a process for amplifying any desired specific nucleic acid sequence contained in a nucleic acid or mixture thereof.

Furthermore, U.S. Pat. No. 5,593,824 and U.S. Pat. No. 5,763,157 (Treml) describe biological reagent spheres useful for the PCR reaction. Additionally, this invention describes a convenient approach by means of excipient mixes comprising suitable carbohydrates useful for storage of reagents used in downstream genetic analysis such as PCR. Carbohydrates are preferably Ficoll and melezitose. This technology has been commercialised in a ready to go (RTG) PCR format (GE Healthcare).

Long-term storage, transport and archiving of nucleic acids on filter paper or chemically modified matrices is a well-known technique for preserving genetic material before the DNA or RNA is extracted and isolated in a form for use in genetic analysis such as PCR. Thus, EP 1563091 (Smith et al, Whatman) relates to methods for storing nucleic acids from samples such as cells or cell lysates. The nucleic acid is isolated and stored for extended periods of time at room temperature and humidity, on a wide variety of filters and other types of solid phase media. This invention describes methods for storing nucleic acid-containing samples on a wide range of solid phase matrices in tubes, columns, or multiwell plates.

Cellulose derived matrices are described by reference to the following prior art. WO 1990/003959 (Burgoyne) describes a solid medium for the storage of DNA, including blood DNA, comprising a solid matrix having a compound or composition which protects against degradation of DNA incorporated into or absorbed on the matrix. This patent also discloses methods for storage of DNA using this solid medium, and for recovery of DNA or in situ use of DNA.

U.S. Pat. No. 5,496,562 (Burgoyne) describes a solid medium and method for DNA storage. This invention relates to a solid medium for use in the storage of DNA and to methods which comprise the use of this solid medium. In particular, this invention relates to a method for storage and transport of DNA on the solid medium, as well as to methods which involve either (a) the recovery of the DNA from the solid medium or (b) the use of the DNA in situ on the solid medium (for example, DNA sequence amplification by a polymerase chain reaction-PCR).

Forensic and Human Identification Applications

DNA profiling (also called DNA testing, DNA typing, or genetic fingerprinting) is a technique employed by forensic scientists to assist in the identification of individuals by their respective DNA profiles. DNA profiles are encrypted sets of numbers that reflect a person's DNA makeup, which can also be used as the person's identifier. DNA profiling should not be confused with full genome sequencing. It is used in, for example, parental testing and criminal investigations.

The method of DNA profiling used is based on PCR and uses short tandem repeats of nucleotide sequences. This method uses highly polymorphic regions that have short repeated sequences of DNA (the most common is 4 bases repeated, but there are other lengths in use, including 3 and 5 bases). Because unrelated people almost certainly have different numbers of repeat units, STRs can be used to discriminate between unrelated individuals. These STR loci (locations on a chromosome) are targeted with sequence-specific primers and amplified using PCR. The DNA fragments that result are then separated and detected using electrophoresis. There are two common methods of separation and detection, capillary electrophoresis (CE) and gel electrophoresis.

Each STR is polymorphic, but the number of alleles is very small. Typically each STR allele will be shared by around 5-20% of individuals. The power of STR analysis comes from looking at multiple STR loci simultaneously. The pattern of alleles can identify an individual quite accurately. Thus STR analysis provides an excellent identification tool. The more STR regions that are tested in an individual the more discriminating the test becomes.

From country to country, different STR-based DNA-profiling systems are in use. In North America, systems which amplify the CODIS 13 core loci are almost universal, while in the UK the SGM+ 11 loci system (which is compatible with The National DNA Database), is in use. Whichever system is used, many of the STR regions used are the same. These DNA-profiling systems are based on multiplex reactions, whereby many STR regions will be tested at the same time.

The true power of STR analysis is in its statistical power of discrimination. Because the 13 loci that are currently used for discrimination in CODIS are independently assorted (having a certain number of repeats at one locus doesn't change the likelihood of having any number of repeats at any other locus), the product rule for probabilities can be applied. This means that if someone has the DNA type of ABC, where the three loci were independent, we can say that the probability of having that DNA type is the probability of having type A times the probability of having type B times the probability of having type C. This has resulted in the ability to generate match probabilities of 1 in a quintillion ($1 \times 10^{18}$) or more. However, DNA database searches have shown much more frequent than expected false DNA profile matches. Moreover, since there are about 12 million monozygotic twins on Earth, the theoretical probability is not accurate.

In the USA, military personnel are required to submit genetic samples to the Department of Defence for entry into the Pentagon's DNA database. The creation of the database was prompted in part by the challenge the military faced in identifying human remains during the first Gulf War, and its acknowledged purpose is to expedite identification of human remains in future conflicts. Military customers currently use dry storage cards to database DNA samples from their soldiers.

The US military has been data-basing every soldier's DNA since 1992. The total database which is located in Dover, Del., USA, now exceeds a total of 6 million realising the benefits of reliable human identification from the engagement of collection cards and the possible storage of human genetic information. The total number of military personnel worldwide is 19 million with the top 5 militaries accounting for more than 40% of this Group.

Thus, the present invention addresses military data basing of DNA samples for use in deceased identification. It is clear that there is a need from the Military for a substantive solution in addition to simple blood or buccal cell cards. Currently, the military are seeking a secure method of tracking of collection cards, organising the data associated with each card, and properly storing the cards for long-term access. This is particularly important where DNA sample cards may be initially housed in haphazard fashion. Embodiments of this invention address these needs, by linking biometric and electronic data storage and retrieval in a simple, accessible form on dry substrates designed for long term storage of genetic material at ambient temperature and useful for, but not limited to human identification, military and clinical applications. This disclosure also describes the use, and novel methods for processing the biometric device described herein.

In addition to storage and retrieval of genetic and electronic information, the electronic tagging system described herein can also be used to manage data and samples, aid complex methods and to direct steps of an analysis or processing techniques with reduced delays. The present invention can also reduce manual data entry and sample sorting upon storage and when carrying out downstream processing and applications by the use of an RFID tag in association with a dry storage matrix.

US 2009-0318751 (IVF Ltd) describes a chamber based apparatus for communicating with a memory tag and use of the same e.g. for the identification of sperm, eggs and embryos stored in sample vessels at low temperatures.

US 2011-0199187 (Biotillion) describes biological and other samples using RFID tags stored in liquid nitrogen dewers in vials. This method has a number significant disadvantages including cooling, risk of injury, installation of expensive equipment and high maintenance and running costs.

US 2009-0298132 (Muller-Cohn) describes the composition and methods for automated storing, tracking and analysing biological samples using dissolvable dry storage matrices.

US 2008-0176209 (Biomatrica) describes the integration of sample storage and sample management for life science using dissolvable dry storage matrices.

US 2011-0212859 (Life Technologies) describes radio frequency identifiers for use in biological science. This disclosure describes a complex biological research method, kit and product that utilizes radio frequency identifier technology on passive chips, vessels arrays or tubes, but not using dry inert substances for the long term storage of genetic material or information, and, not for human identification or clinical purposes as described herein.

SUMMARY OF THE INVENTION

According to a first aspect the invention provides a biometric device, comprising a solid support suitable for receiving biological material and for dry storing that material at room temperature the device further comprising a circuit including means for two way radio frequency communication and including writable data storage.

According to a second aspect, the invention provides a storage system for storing plurality of biometric devices each containing biological material, the system comprising: a) bringing together a plurality of biometric devices according to the first aspect; b) housing each device in spaced relation; and c) identifying one or more of said housed devices by means of interrogating its associated circuit using RF communication.

According to a third aspect, the invention provides a method for the processing of a biometric device comprising a solid support suitable for receiving biological material and for dry storing that material at room temperature the device further comprising a circuit including means for two way radio frequency communication and including writable data storage, the method including the steps of: a) identifying said device by means of RF communication; b) extracting at least a portion of the biological material from the solid support of the identified device; c) analysing the extracted biological material to obtain biometric data indicative of the biological material; and d) writing said biometric data to the data storage of the biometric device.

Preferred features of the invention are set out in the dependant claims appended hereto.

DETAILED DESCRIPTION OF THE INVENTION

The present invention describes a novel device and method for the simple electronic tagging of biological materials on solid support matrices, such as cellulose-based paper (e.g. chemically modified or unmodified paper, nitrocellulose, chemically modified nitrocellulose, membranes, nylon, PVDF and the like), together with a large number of different applications, including forensics, military, human identifications and clinical applications that require long term storage and retrieval of biological and genetic information.

Figure 1A:
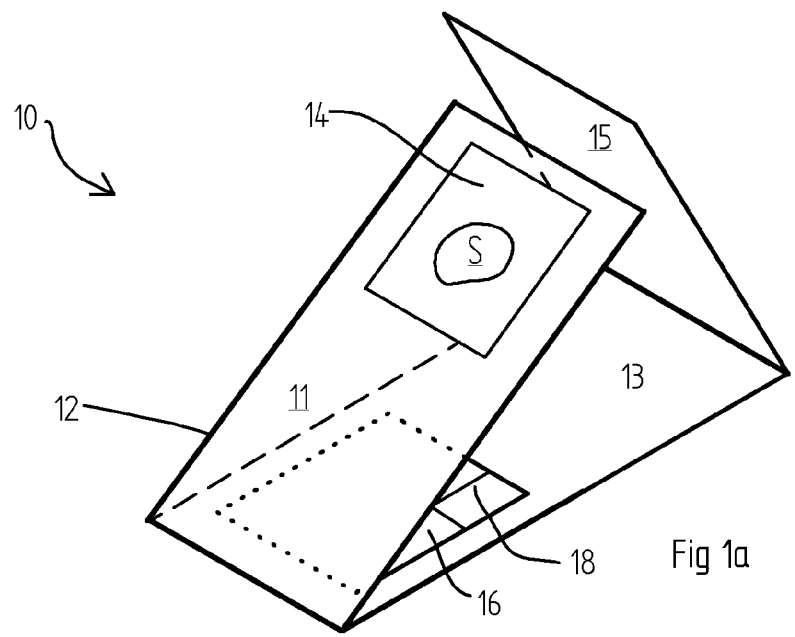
FIGS. 1a and 1b show a first embodiment of a device according to the invention.

Referring to FIG. 1 there is shown a biometric device 10 in the form of a foldable card support 12, holding a solid support 14, in this case a sheet of cellulose paper chemically coated and dried (known commercially as FTA®) for accepting and preserving a biological sample S, the support 12 also supports an RFID device or tag 16. A tag antenna 18 is supported also on the support 12. In FIG. 1a the card is shown unfolded.

Figure 1B:
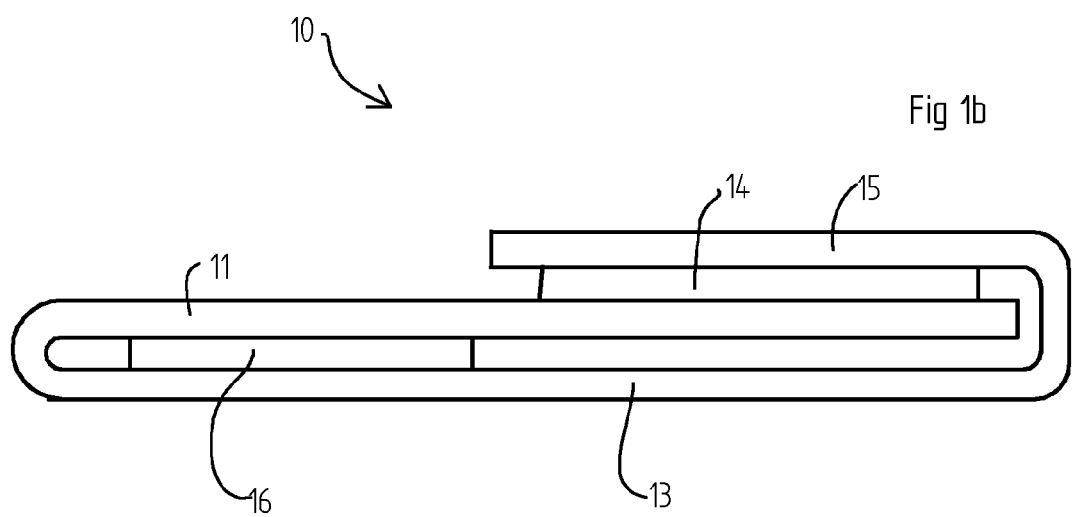

In FIG. 1b, the card 12 shown folded. A mid portion 13 holds the tag 16, a first end portion 11 holds the solid matrix and is folded onto the mid portion 13, and a second end portion 15 which is folded over the first end to cover the solid matrix, to protect it from contamination. In use, a sample of biological material, is manually deposited on the solid matrix, and allowed to dry then the second end portion 15 is folded onto the solid support 14. The card is identified by physically marking the card. Further processing of the device is detailed below.

Figure 2A:
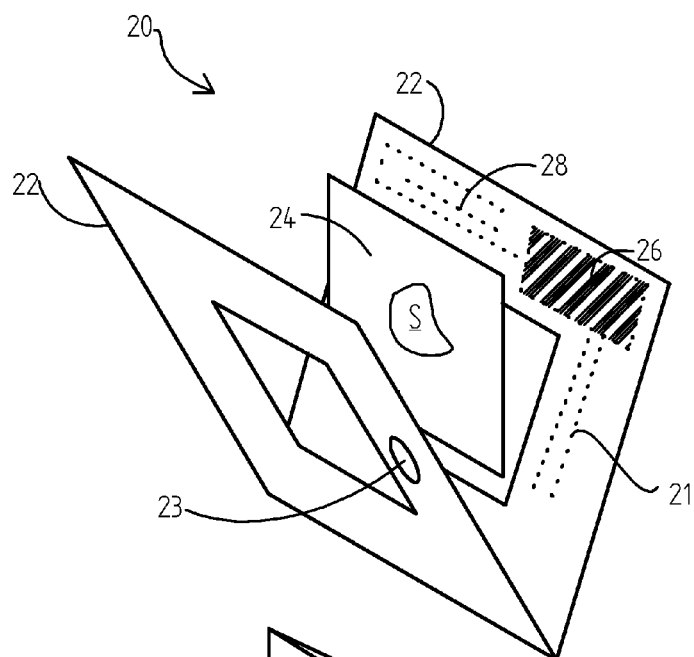
FIGS. 2a and 2b show a second embodiment of a device according to the invention.

FIG. 2a shows an exploded view of an alternative biometric device 20. This device comprises frame 22, and a biological sample collection area 24 in the form of a solid support matrix of FTA material. In this embodiment, the frame 22 surrounds the matrix 24 and has two similar halves which sandwich the matrix 24. The halves and held together, and hold the matrix in place by means of adhesive applied to the frame and or the matrix. As well as the matrix, an RFID tag 26 is also held between the opposing halves 22 of the frame, and an antenna 28 for the tag is also so held.

A biological sample material S is deposited on the matrix 24. The device includes also a conductive path 21 connected to the tag 26 in such a way that the tag can recognise the conductivity of the path 21. The frame has a weakness 23 which can be broken by a user, which in turn breaks the conductive path 21. So once a biological sample has been applied to the matrix a user can signal this occurrence to the tag by breaking the frame at the weakness 23. The matrix is allowed to dry and the device is inserted into a protective sleeve 25 for transport. The device can be processed further as described below.

Figure 2A:
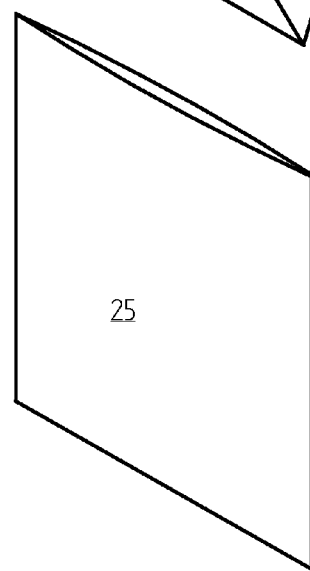
Figure 2B:
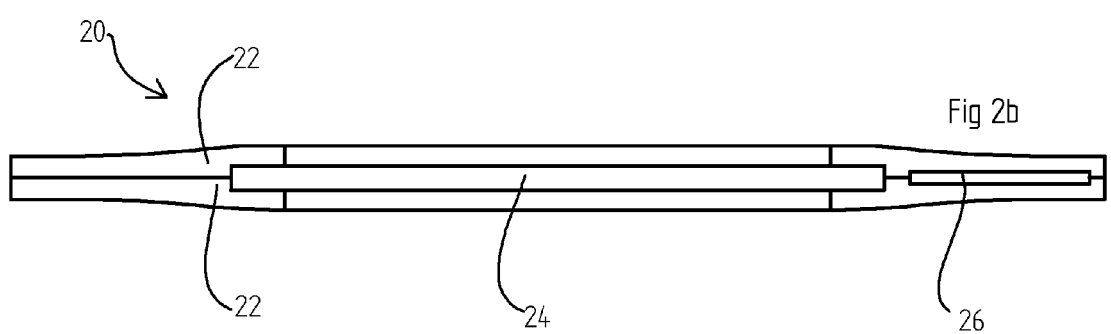

In the description of FIGS. 1 and 2 specific materials are referred to, however, it will be readily apparent that other material could be used for supporting surfaces. For example card could be replaced with plastics or metal materials or could be manufactured completely from the FTA material mentioned. Whilst the commercially available FTA paper is preferred as a biological sample solid support storage matrix, other materials could be employed.

In the two embodiments mentioned above the devices 10/20 are intended to store biometric material, for example the DNA from whole blood drawn from an individual, in the form of dried blood spots. Simultaneously, personal information is electronically stored on the RFID tag associated with the sample collection card. It is envisaged that such cards will be sorted in individual pouches and shipped to a central laboratory. Deskilled personnel will then organise the cards via an electronic reader and information is submitted into a database. The pouches will then be stored securely in storage units The storage units will be equipped with RFID tag readers that will detect the position of each card within the storage unit so that the appropriate card may be tracked and will be readily retrieved. Blood sample testing of the genetic information on the card by STR analysis will then readily confirm the identity of any human remains tested in the same way.

The current invention has many advantages over the prior art that typically uses bar code because readers and information may be exchanged or re written to the storage device. Furthermore, data may be readily exchanged with the electronic database stored on a remote computer or mainframe.

This invention also describes the addition of an electronic tag (e.g. radio-frequency identification (RFID) tag) to a storage device which accelerates the collection of soldier/personal data in the field, while reducing the staff/time needed to process incoming cards at a central laboratory or processing unit. It is envisaged that the device 10/20 will be stored in a vertical cabinet, or rack that maximizes storage capacity and tracks the presence of each card inside. Additionally, the inventors have proposed software that will act alone or as a tracking mechanism or interface with the military's existing health systems. Such tracking can be done intermittently, for example by an electronic audit of the device in the storage cabinet or rack.

The invention described here could also be useful in cancer research and treatment bio banking. It also may provide applications in universal patient tracking for mass casualty incident responses and covers all card types/swabs used for biological sample collection and storage.

This invention is also useful for felon identification, and may be useful to the databases such as The Fichier National Automatisé des Empreintes Génétiques (Automated National File of Genetic Prints) (FNAEG) is the French national DNA database, used by both the national French police force and local gendarmerie, which are known to use FTA®. As at Oct. 1, 2003, FNAEG was understood to contain the DNA records of approximately 8,000 convicted criminals and another 3,200 suspects. In December 2009, there were 1.27 million entries on the French police database.

Similarly, the United Kingdom National DNA Database (NDNAD; officially the UK National Criminal Intelligence DNA Database) is a national DNA Database that was set up in 1995. As of the end of 2005, it carried the profiles of around 3.1 million people. This database, grows approximately by 30,000 samples each month, is populated by samples recovered from crime scenes and taken from police suspects and, in England and Wales, anyone arrested and detained at a police station. The total number of individuals' data retained on the NDNAD about 6.6 million. Individuals' skin or blood samples are also kept permanently linked to the UK database and this contains complete genetic information. The UK database typically uses Omniswab. Because DNA is inherited, the database can also be used to indirectly identify many others in the population related to a database subject. Stored samples can also degrade and become useless, particularly those taken with dry brushes and swabs, so in this case an OmniSwab/RFID device may offer advantages to such databases.

Clinical Applications

A number of DNA databases created from babies' blood samples also exists. Blood samples taken in heel-prick tests to screen for serious conditions are being held for years by some hospitals and can be subsequently accessed by the police to identify people involved in crimes. The samples can also be used by coroners and medical researchers for a variety of purposes. Blood spot screening is carried out on babies aged between five and eight days old in order to test for a variety of serious conditions such as cancer, tumour marking and archiving, sickle cell, PKU and cystic fibrosis. Government guidelines advise hospitals to store the samples for at least five years before destroying them. The device described here may have additional applications for identification storage and retrieval of neonatal cards spotted with blood from neonates and stored in hospitals. Thus the electronic device could be adapted to be used with neonatal screening cards. In Denmark, for example, the Danish Newborn Screening Biobank at Statens Serum Institut retains a blood sample from all neonates born after 1981. The purpose is to test for PKU and other diseases. This database is also used for DNA tests to identify deceased and suspected criminals. In addition, the invention described here would act as a system for tracking and managing animals and/or food products, and potentially may be useful in paternity testing cases Electronic Tags RFID is the use of a wireless non-contact system that uses electromagnetic fields generated by radio-frequency energy (in the range of 3 Hz to 3000 GHz) to transfer data from an enclosed circuit and antenna (an RFID 'tag') attached to an object, for the purposes of automatic identification and tracking. Some tags require no battery and are powered by the electromagnetic fields used to read them. Others use a local power source and emit radio waves (electromagnetic radiation at radio frequencies). The tag contains electronically stored data which can be read from up to several meters (yards) away. Unlike a bar code, the tag does not need to be within line of sight of the reader and may be embedded in the tracked object.

In known systems, a radio-frequency identification system uses tags, attached to the objects to be identified. Two-way radio transmitter-receivers called interrogators or readers send a generic signal to the tag and read its response. The readers generally transmit their observations to a computer system running RFID software or RFID middleware.

In this invention, the tag's identification details stored electronically in a non-volatile memory—herein called data storage. The RFID tag circuit includes a small RF transmitter and receiver, for two way communication. An RFID reader transmits an encoded radio signal to interrogate the tag. The tag receives the message and responds with its identification information. Initially, this may be only a unique tag serial number, or other tag-specific information.

The RFID tag described herein can be either passive, active or battery assisted passive. An active tag has an on-board battery and periodically transmits its ID signal. A battery assisted passive (BAP) has a small battery on board and is activated when in the presence of a RFID reader. A passive tag is cheaper and smaller because it has no battery. Instead, the tag uses the radio energy transmitted by the reader as its energy source. The interrogator must be close for RF field to be strong enough to transfer sufficient power to the tag. Since tags have individual serial numbers, the RFID system design can discriminate several tags that might be within the range of the RFID reader and read them simultaneously.

Commercially available tags may either be read-only, having a factory-assigned serial number that is used as a key into a database, or may be read/write, where object-specific data can be written into the tag by the system user. Field programmable tags may be write-once, read-multiple; "blank" tags may be written with an electronic product code by the user. The preferred tag of this invention is either a writable data store meaning it can be populated in use, or rewritable data store which can be populated, added to, or overwritten in use.

Signalling between a reader and the tag can be done in several different ways, depending on the frequency band used by the tag. Tags operating on LF and HF frequencies are, in terms of radio wavelength, very close to the reader antenna, only a small percentage of a wavelength away. In this near field region, the tag is closely coupled electrically with the transmitter in the reader. The tag can modulate the field produced by the reader by changing the electrical loading the tag represents. By switching between lower and higher relative loads, the tag produces a change that the reader can detect. At UHF and higher frequencies, the tag is more than one radio wavelength away from the reader, requiring a different approach. The tag can backscatter a signal. Active tags may contain functionally separated transmitters and receivers, and the tag need not respond on a frequency related to the reader's interrogation signal.

In conventional tags an Electronic Product Code (EPC) is one common type of data stored in a tag. When written into the tag by an RFID printer, the tag contains a 96-bit string of data. The first eight bits are a header which identifies the version of the protocol. The next 28 bits identify the organization that manages the data for this tag; the organization number is assigned by the EPC Global consortium.

The next 24 bits are an object class, identifying the kind of product; the last 36 bits are a unique serial number for a particular tag. These last two fields are set by the organization that issued the tag. Rather like a URL, the total electronic product code number can be used as a key into a global database to uniquely identify a particular product. In the present invention, this data can be overwritten, with biological and personal data mentioned above.

Commercially available methods of avoiding collision of communications between different tags and the reader can be employed. Often more than one tag will respond to a tag reader, for example, many individual products with tags may be shipped in a common box or on a common pallet. Collision detection is important to allow reading of data. Two different types of protocols are used to "singulate" a particular tag, allowing its data to be read in the midst of many similar tags. In a slotted Aloha system, the reader broadcasts an initialization command and a parameter that the tags individually use to pseudo-randomly delay their responses. When using an "adaptive binary tree" protocol, the reader sends an initialization symbol and then transmits one bit of ID data at a time; only tags with matching bits respond, and eventually only one tag matches the complete ID string.

Whilst use in identification of individuals is described above, this invention could be applied generally for the collection, processing, storage and maintenance of biological samples to facilitate long-term cohort studies in bio banks, which normally would require a complex system to manage samples in an effective way to prevent sample mix up and loss. Sample identification and tracking system described here would aim to store data on the samples at all the times. In this instance RFID technology could be readily employed. Therefore, the technology described here would allow information to be stored on the tags effectively attached to biological material.

Figure 3:
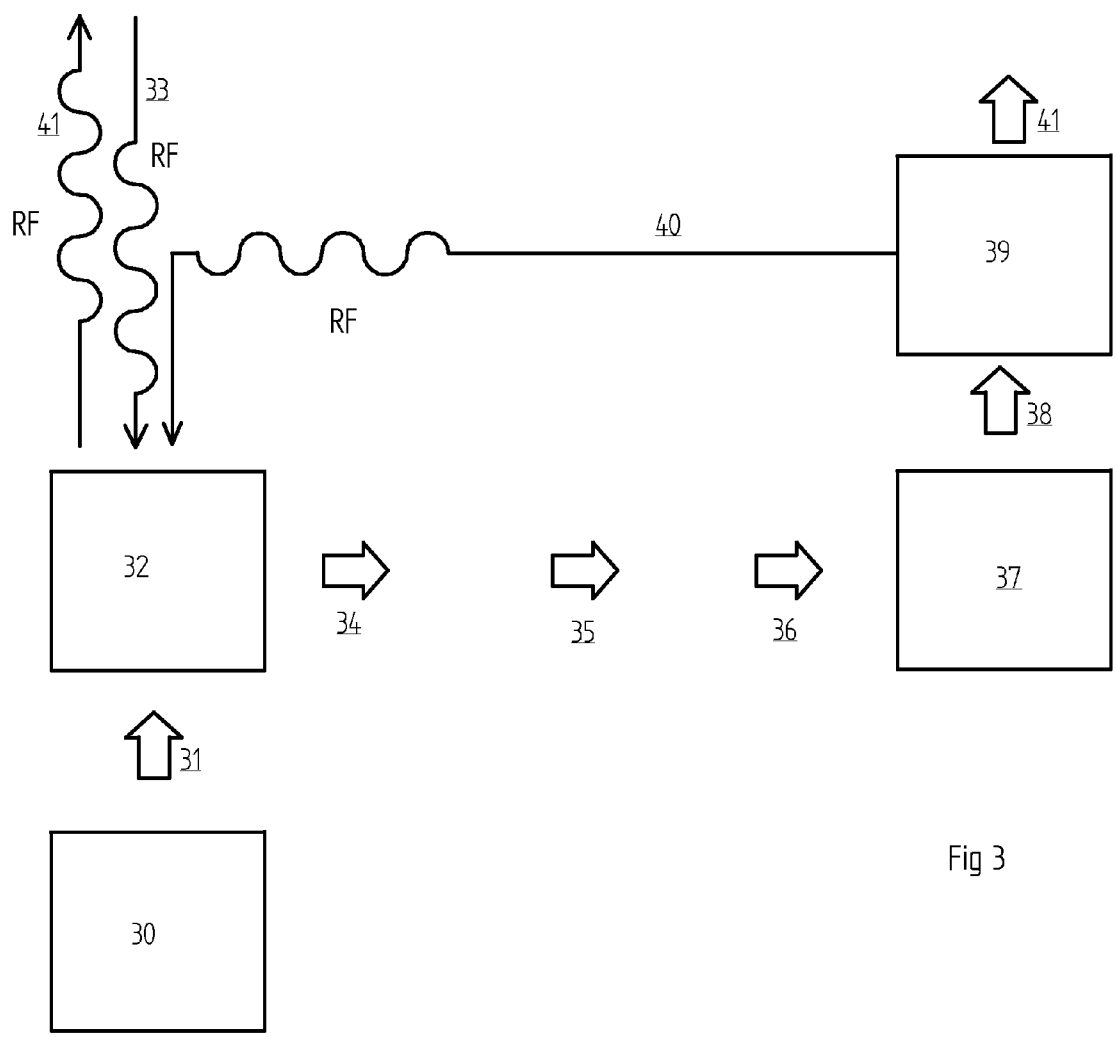
FIG. 3 shows schematically a method employing the devices of FIG. 1 or 2.

FIG. 3 illustrates the processing steps of the devices 10 and 20 mentioned above. In this process the rectangles represent physical attributes, and the arrows represent actions.

Rectangle 30 represents the biometric devices 10 or 20.

Step 31 is the application of a biological sample to the device, for example by means of applying a spot of blood onto the device and the (possibly long delayed) step of sending the device to a testing facility (lab).

Rectangle 32 is the physical retention of the device at the testing lab.

Step 33 represents the recording of personal data onto the RFID tag which is likely to identify the provider of the biological sample and may also include further personal information as detailed above. This step is only required where such data has not been added to the tag's memory previously. This step can be performed using a tag writer which adds information to an RFID memory in the circuit of the RFID tag. If necessary a check can be made to ensure that the conductive path 21 has been broken, thus indicating that a sample has been deposited onto the matrix.

Step 34 represents the punching out of a small piece of the matrix for analysis. It is not necessary to use the whole of the matrix.

Step 35 represents the processing of the piece of matrix under by known PCR techniques to obtain DNA from the sample. In this step, it is preferred that the polymerase chain reaction reagent mixture is present in a dried form, such as a "Ready-to-Go™" (RTG) format. The advantage of dried or lyophilised formulations of the polymerase chain reaction reagents is that they can be easily solublised by the addition of water, thus saving operator time or facilitating automation. To minimise operator error, the dried reagent mixture can be pre-dispensed into the reaction vessel, such as the well of a multi-well plate. Examples of such an RTG mixture include "Illustra Ready-to-Go RT-PCR beads" available from GE Healthcare (product code: 27-9266-01 Illustra Ready-To-GoRT-PCR Beads). These freeze-dried beads that include the reagents necessary for one-step reverse transcription-PCR, can be pre-dispensed into a reaction vessel, such as the well of a multi-well plate, as a single dose ready for use. The preformulated, predispensed, ambient-temperature-stable beads thus ensure greater reproducibility between reactions, minimize pipetting steps, and reduce the potential for pipetting errors and contamination, particularly where no automation is employed. Whilst the process has been described for amplifying DNA or RNA for identification purposes, the amplification could be used for increasing the amount of genetic material from a template for example for use in molecular cloning. The techniques used are described in Sambrook & Russell, Molecular Cloning a Laboratory Manual—Cold Spring Harbor Laboratories Press, 3rd Edition.

Step 36 represents the electrophoresis of the DNA or RNA sample to indicate, for example STR information as mentioned above.

Rectangle 37 represents hardware for scanning the results of the electrophoresis step for digitising that information and turning it into electronic data.

It should be mentioned that step 36 and rectangle 37 could be replaced with other analysis techniques and hardware which are known in the art, for example, viral diagnostics, testing for genetic markers, and oncogene detection for cancer treatment. In each case the relevant electronic data can be obtained from known analysis techniques. Other specific tests could include the detection of proteins for example immunoreactive trypsin (IRT) in dried blood spots for neonatal screening for cystic fibrosis (CF). A sensitive, human trypsin immunoassay, which uses a 3-mm diameter disc punched from the medium and holding a dried blood. Such a test is described in 'Neonatal screening for cystic fibrosis, using immunoreactive trypsin assay in dried blood spots'; Crossley et al, 1981, Clin Chim Acta 113 (3) 111-121). Other protein detection methods could be used to diagnose other disease states.

Step 38 is the transmission of the relevant data to a RFID tag writer.

Rectangle 39 is an RFID tag writer which can write data to the tag in a known form.

Step 40 is the writing of the electronic data to the tag represented by rectangle 32, by means of RF signalling.

Step 41 is the copying of the said data to a database where this is permitted, again by means of RF signalling.

From FIG. 3 it can be seen that data obtained from genetic testing of the biological material sample on the biometric device can be stored on the device along with personal information of the sample provider.

This data, biological material and personal information (together called biometric information) can be held together without the need for it to be placed on a searchable central database. So the privacy for the sample provider can be maintained, and records are less likely to become lost or corrupted.

Whilst the device and methods for recording the biometric information on the device have been described in relation to personal identification, this application should not be considered to be limiting. As mentioned above the biometric device can be used in connection with, for example cancer diagnosis and therapy, and so the device then functions as a patient record. Future testing can be compared to samples collected previously, and there is no need for the biometric data contained on one or more devices to be stored on a remote database.

Specifically methods disclosed herein may comprise purifying amplified nucleic acid and/or cloning the amplified nucleic acid. Also, the methods may include use as a tool selected from the group consisting of a molecular diagnostics tool, a microbial identification tool, a human identification tool, a genetic testing tool a tissue typing tool and a forensics tool. Also, the biological data written to the circuit mentioned herein may include data relating to repeating sequences of DNA base pairs (STR). Such data, written to the data storage of the circuit, can be further recorded at a remote database. It will be understood that biological material should be immobilised on the solid support, preferably for at least 2 hours following its receipt on the support. It is envisaged that the biological material comprises eukaryotic or prokaryotic cellular material. Preferably the biological material is a cellular sample selected from the group consisting of: blood; saliva; urine; faeces; hair; skin; tissue; muscle; cell culture samples; buccal cells, cervical cells; cervical samples; microbial cells; tumour cells; stem cells; pathogens; bacteria; viruses; and fungi. Methods according to the invention include a protein binding assay, an immunoassay, an analysis for providing epigenetic information, or an antibody or enzyme detection system. Kits may be provided for carrying out assays or analyses, and may contain a biometric device as described above and a dried reagent mix and/or a swab or other sample collection device for transferring biological material onto the device.

What is claimed is:
1. A biometric information storage device comprising:
a foldable card support comprising a first region, a second region, and a third region, wherein a first fold in the card support separates the first region from the second region, and wherein a second fold in the card support separates the second region from the third region,
wherein the first region comprises a solid support configured to receive a biological sample, dry store the biological sample at room temperature, and allow retrieval of the biological sample therefrom, and wherein the solid support is a cellulose-based paper matrix chemically treated with:
  i) a weak alkali;
  ii) a chelating agent;
  iii) an anionic surfactant or detergent; and
  iv) uric acid or a urate salt;
wherein the second region comprises a radio frequency identification (RFID) tag arranged to provide two-way communication and store biometric information in non-volatile memory, and
wherein the foldable card support is configured to be folded such that the third region can at least partially cover the first region and protect a biological sample from contamination when disposed on the solid support.
2. The biometric device of claim 1, wherein the non-volatile memory is rewritable.
3. The biometric device of claim 1, wherein a biological sample is disposed on the solid support, wherein the RFID tag has stored therein personal information relating to a person from which the biological sample is derived, and wherein the RFID tag has stored therein data indicative of the biological sample.

* * * * *